United States Patent
Harrison, IV et al.

(10) Patent No.: US 10,335,126 B2
(45) Date of Patent: Jul. 2, 2019

(54) BONE MARROW ASPIRATION NEEDLE ASSEMBLY

(71) Applicant: ARTHREX, INC., Naples, FL (US)

(72) Inventors: Robert M. Harrison, IV, Naples, FL (US); Robert Benedict, Fort Meyers, FL (US)

(73) Assignee: ARTHREX, INC., Naples, FL (US)

( * ) Notice: Subject to any disclaimer, the term of this patent is extended or adjusted under 35 U.S.C. 154(b) by 251 days.

(21) Appl. No.: 14/446,734

(22) Filed: Jul. 30, 2014

(65) Prior Publication Data
US 2016/0030013 A1 Feb. 4, 2016

(51) Int. Cl.
*A61B 10/02* (2006.01)
*A61B 10/04* (2006.01)

(52) U.S. Cl.
CPC ........ *A61B 10/025* (2013.01); *A61B 10/0283* (2013.01); *A61B 10/04* (2013.01); *A61B 2010/0258* (2013.01); *A61B 2010/045* (2013.01)

(58) Field of Classification Search
None
See application file for complete search history.

(56) References Cited

U.S. PATENT DOCUMENTS

| | | | |
|---|---|---|---|
| 4,177,797 A * | 12/1979 | Baylis | A61B 10/025 600/567 |
| 5,217,463 A * | 6/1993 | Mikhail | A61B 17/02 606/53 |
| 5,257,632 A * | 11/1993 | Turkel | A61B 10/025 600/567 |
| 5,643,202 A * | 7/1997 | Gravenstein | A61H 35/04 604/514 |
| 5,954,671 A * | 9/1999 | O'Neill | A61B 17/1637 600/567 |
| 6,110,128 A | 8/2000 | Andelin et al. | |
| 6,217,557 B1 * | 4/2001 | Hakansson | A61B 17/3415 604/158 |
| 6,221,029 B1 | 4/2001 | Mathis et al. | |
| 7,699,850 B2 | 4/2010 | Miller | |
| 7,850,651 B2 | 12/2010 | Allee et al. | |
| 8,070,690 B2 | 12/2011 | Ikehara et al. | |
| 8,343,133 B2 | 1/2013 | Allee et al. | |
| 8,419,683 B2 | 4/2013 | Miller et al. | |
| 8,486,077 B1 * | 7/2013 | Kornel | A61B 17/1659 606/279 |
| 8,690,791 B2 | 4/2014 | Miller | |
| 2002/0042581 A1 * | 4/2002 | Cervi | A61B 10/025 600/567 |
| 2003/0130664 A1 * | 7/2003 | Boucher | A61B 17/1631 606/86 R |
| 2003/0191414 A1 * | 10/2003 | Reiley | A61B 17/3417 600/567 |
| 2007/0016100 A1 * | 1/2007 | Miller | A61B 10/025 600/567 |

(Continued)

*Primary Examiner* — Matthew Kremer
(74) *Attorney, Agent, or Firm* — Carlson, Gaskey & Olds

(57) ABSTRACT

A needle assembly according to an exemplary aspect of the present disclosure includes, among other things, a cannula, a trocar insertable through the cannula, the trocar including a shaft extending longitudinally between a proximal portion and a tip portion and a groove formed in the shaft and extending from near the tip portion at least partially toward the proximal portion.

18 Claims, 7 Drawing Sheets

(56) References Cited

U.S. PATENT DOCUMENTS

| | | | |
|---|---|---|---|
| 2009/0131827 A1* | 5/2009 | Crocker | A61B 10/025 600/571 |
| 2010/0084453 A1* | 4/2010 | Hu | A61B 17/1155 227/179.1 |
| 2011/0202064 A1* | 8/2011 | O'Halloran | A61B 17/1671 606/94 |
| 2012/0035501 A1 | 2/2012 | Landrigan et al. | |
| 2013/0131545 A1 | 5/2013 | Azimpoor et al. | |
| 2013/0204160 A1 | 8/2013 | McKenna et al. | |
| 2014/0213931 A1* | 7/2014 | Lee | A61B 10/0233 600/567 |

\* cited by examiner

BONE MARROW ASPIRATION NEEDLE ASSEMBLY

BACKGROUND OF THE INVENTION

This disclosure relates to a surgical device. More particularly, this disclosure is directed to a bone marrow aspiration needle assembly for collecting a bone marrow sample for analysis.

Bone marrow is the soft tissue located inside bones that helps form blood cells. Bone marrow is typically located in the hollow parts of most bones. Bone marrow examination is useful for diagnosing a variety of diseases and conditions. A sample of the bone marrow must be first extracted from the bone marrow space before it can be examined.

In one known bone marrow aspiration or biopsy procedure, a needle assembly is inserted into a bone, such as into the posterior iliac crest of the pelvic bone. After the needle assembly penetrates the bone, a trocar or stylet is removed from the needle assembly. Fluid from the bone marrow cavity can then be aspirated through the needle assembly to collect a bone marrow sample, which can then be appropriately analysed. The process of removing the bone marrow sample from bone is often a relatively painful procedure.

SUMMARY OF THE INVENTION

A needle assembly according to an exemplary aspect of the present disclosure includes, among other things, a cannula, a trocar insertable through the cannula, the trocar including a shaft extending longitudinally between a proximal portion and a tip portion and a groove formed in the shaft and extending from near the tip portion at least partially toward the proximal portion.

In a further non-limiting embodiment of the foregoing assembly, the groove extends across an entire length of the trocar.

In a further non-limiting embodiment of either of the foregoing assemblies, the groove extends from the tip portion to the proximal portion.

In a further non-limiting embodiment of any of the foregoing assemblies, the tip portion includes a pointed tip.

In a further non-limiting embodiment of any of the foregoing assemblies, the cannula is removably connected to a handle.

In a further non-limiting embodiment of any of the foregoing assemblies, the trocar includes a central lumen that accommodates a wire.

In a further non-limiting embodiment of any of the foregoing assemblies, the cannula includes a plurality of depth markings and a plurality of side ports.

In a further non-limiting embodiment of any of the foregoing assemblies, the cannula includes a distal portion having a forked tip.

In a further non-limiting embodiment of any of the foregoing assemblies, the trocar includes a cap and the shaft is connected to the cap.

In a further non-limiting embodiment of any of the foregoing assemblies, an adaptor is disposed on the cap and configured to receive an insertion tool.

A bone marrow aspiration needle assembly according to another exemplary aspect of the present disclosure includes, among other things, a handle, a cannula removably connected to the handle and a trocar insertable into the cannula, the trocar including a groove that extends along a shaft and a cap that includes an adaptor configured to accommodate an insertion tool.

In a further non-limiting embodiment of the foregoing assembly, the cannula is connected to the handle by a coupling assembly.

In a further non-limiting embodiment of either of the foregoing assemblies, the groove extends an entire length between a tip portion and a proximal portion of the trocar.

In a further non-limiting embodiment of any of the foregoing assemblies, the adaptor includes a plurality of pin openings.

In a further non-limiting embodiment of any of the foregoing assemblies, the adaptor includes a recessed opening having a hexagonal shape.

A surgical method according to another exemplary aspect of the present disclosure includes, among other things, inserting a needle assembly into a bone marrow space inside a bone, the needle assembly including a cannula and a grooved trocar received through the cannula, and equalizing a pressure gradient between the bone marrow space and an ambient space outside of the bone with the grooved trocar as the grooved trocar is removed from the cannula.

In a further non-limiting embodiment of the foregoing surgical method, the inserting step includes connecting an insertion tool to an adaptor of the grooved trocar and drilling the needle assembly into the bone marrow space.

In a further non-limiting embodiment of either of the foregoing surgical methods, the method includes disconnecting a cap of the grooved trocar from a handle of the needle assembly prior to removing the grooved trocar from the cannula.

In a further non-limiting embodiment of any of the foregoing surgical methods, the method includes inserting an extraction tool into the cannula after removing the grooved trocar.

In a further non-limiting embodiment of any of the foregoing surgical methods, the inserting step includes positioning the needle assembly over a wire via a central lumen that extends through the grooved trocar.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

This disclosure details a bone marrow aspiration needle assembly that can be utilized to obtain a bone marrow sample. In some embodiments, the needle assembly includes a trocar having a shaft and a groove extending longitudinally along the shaft. In other embodiments, the needle assembly includes a trocar having a cap that includes an adapter configured to accommodate an insertion tool, such as a drill. In still other embodiments, the needle assembly includes a handle and a cannula removably connected to the handle. These and other features are described in greater detail in the paragraphs that follow.

Figure 1:
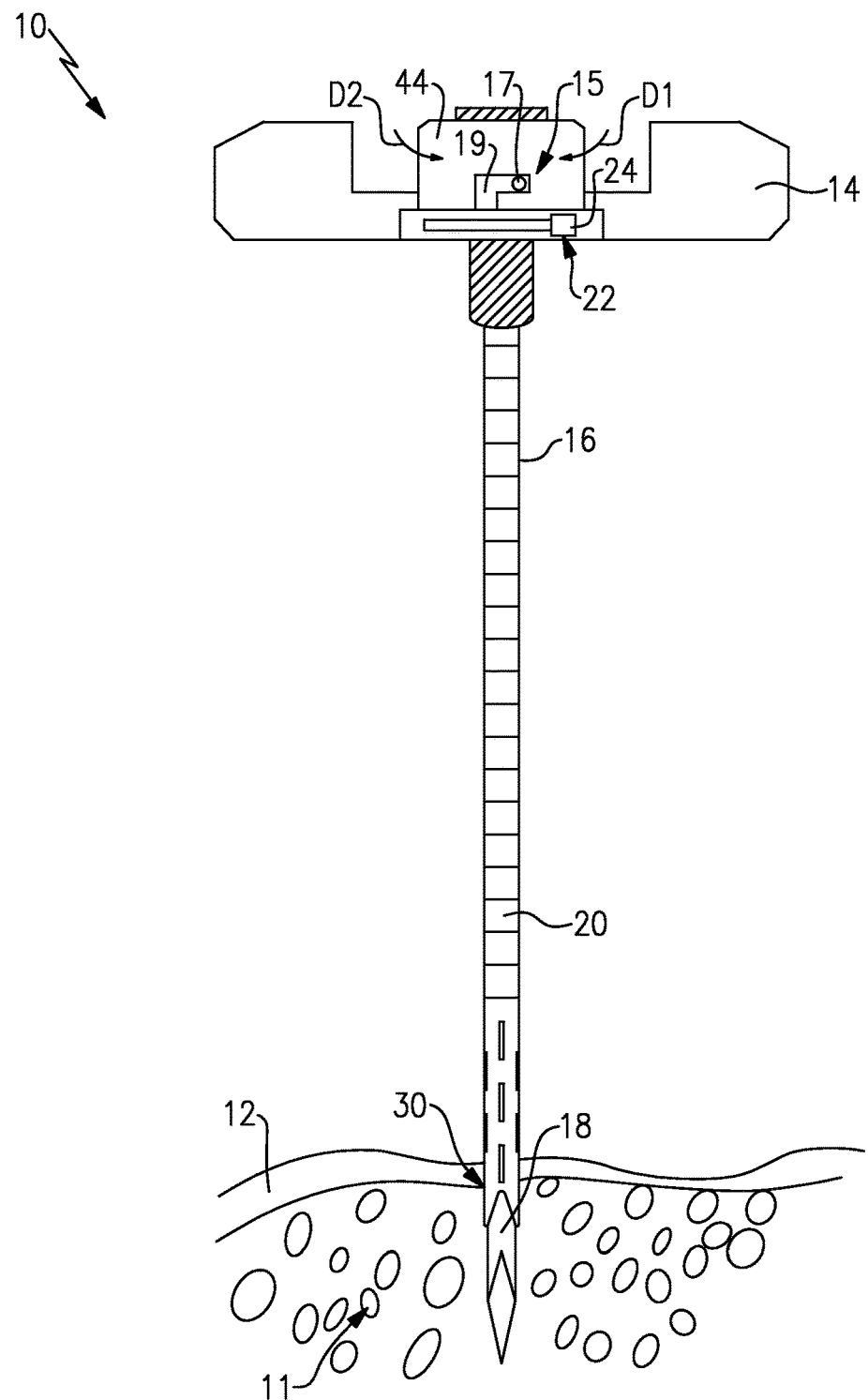
FIG. 1 illustrates a bone marrow aspiration needle assembly.

FIG. 1 illustrates a bone marrow aspiration needle assembly 10. The needle assembly 10 may be employed to harvest a bone marrow sample from a bone marrow space 11 inside a bone 12. The exemplary needle assembly 10 may be used to perform biopsies of soft tissue or bone. In one non-limiting embodiment, the bone 12 is a pelvic bone, and the needle assembly 10 may be inserted into the posterior iliac crest of the pelvic bone. However, the needle assembly 10 could be used to aspirate bone marrow samples from other locations of a patient's body, including the breast bone, sternum, tibia and/or any other bone.

The needle assembly 10 may include a handle 14, a cannula 16 connected to the handle 14, and a trocar 18 insertable through the cannula 16. The trocar 18 may be received through an internal bore 20 of the cannula 16 and may extend beyond a distal portion 30 of the cannula 16. In one embodiment, the cannula 16 is removably connected to the handle 14 via a coupling assembly 22. The coupling assembly 22 may include an actuator 24 that can be actuated to release the cannula 16 from the handle 14.

In another embodiment, the trocar 18 is removably connected to the handle 14. The trocar 18 may be connected to the handle 14 using a luer-type coupling 15. The luer-type coupling 15 may include a tab 17 and an L-shaped notch 19 for receiving the tab 17. In one embodiment, the tab 17 is part of the handle 14 and the notch 19 is part of a cap 44 of the trocar 18. An opposite configuration is also contemplated in which the tab 17 is part of the cap 44 and the notch 19 is part of the handle 14. The cap 44 of the trocar 18 may be twisted in a first direction D1 to connect the trocar 18 to the handle 14, and may be twisted in a second, opposite direction D2 to disengage the trocar 18 from the handle 14, in one non-limiting embodiment.

Figure 2:
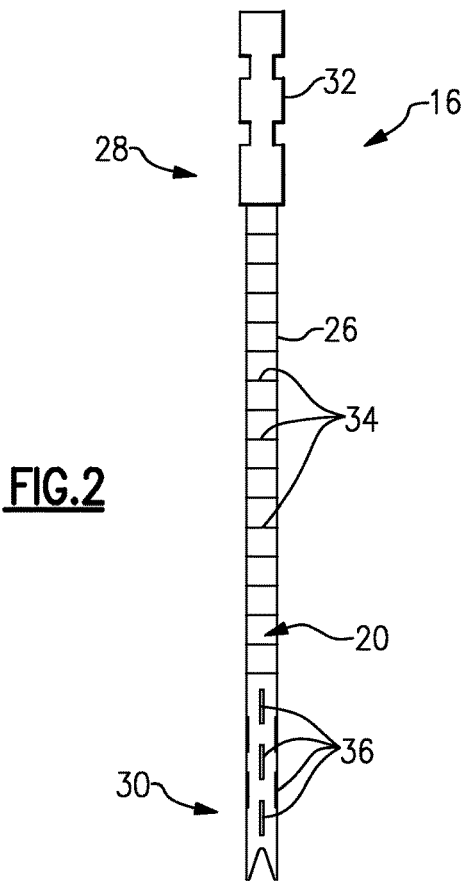
FIG. 2 illustrates a cannula of a bone marrow aspiration needle assembly.

FIG. 2 illustrates a cannula 16 of the bone marrow aspiration needle assembly 10 of FIG. 1. The cannula 16 includes a tube 26 that extends between a proximal portion 28 and a distal portion 30. The proximal portion 28 includes a hub 32 configured to connect to the coupling assembly 22 of the handle 14 (see FIG. 1). A plurality of depth markings 34 may be disposed along a length of the tube 26. The depth markings 34 can be used to control a depth of insertion of the needle assembly 10 into the bone 12 (see FIG. 1).

The cannula 16 may additionally include multiple side ports 36 that extend through the tube 26. In one embodiment, the side ports 36 are disposed along a length of the tube 26 between the distal portion 30 and the depth markings 34. The side ports 36 may embody a variety of sizes and shapes. The side ports 36 open into the internal bore 20 of the cannula 16 and may reduce pressure during a bone marrow aspiration process. This may reduce inefficient bone marrow flow through the internal bore 20 and damage to the bone marrow as it is aspirated through the needle assembly 10.

Figures 3A, 3B:
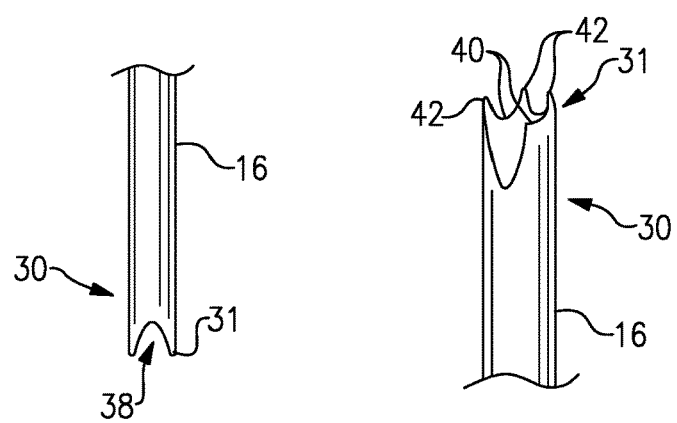
FIGS. 3A and 3B illustrate exemplary distal portions of a cannula of a bone marrow aspiration needle assembly.

FIG. 3A illustrates a first embodiment of a distal portion 30 of the cannula 16. In this embodiment, the distal portion 30 includes a forked tip 31 having at least one V-shaped notch 38. In another embodiment, shown in FIG. 3B, the distal portion 30 includes a forked tip 31 that includes a plurality of indents 40. The indents 40 may form serrated edges 42. The serrated edges 42 facilitate the insertion of the needle assembly 10 into bone 12.

Figure 4:
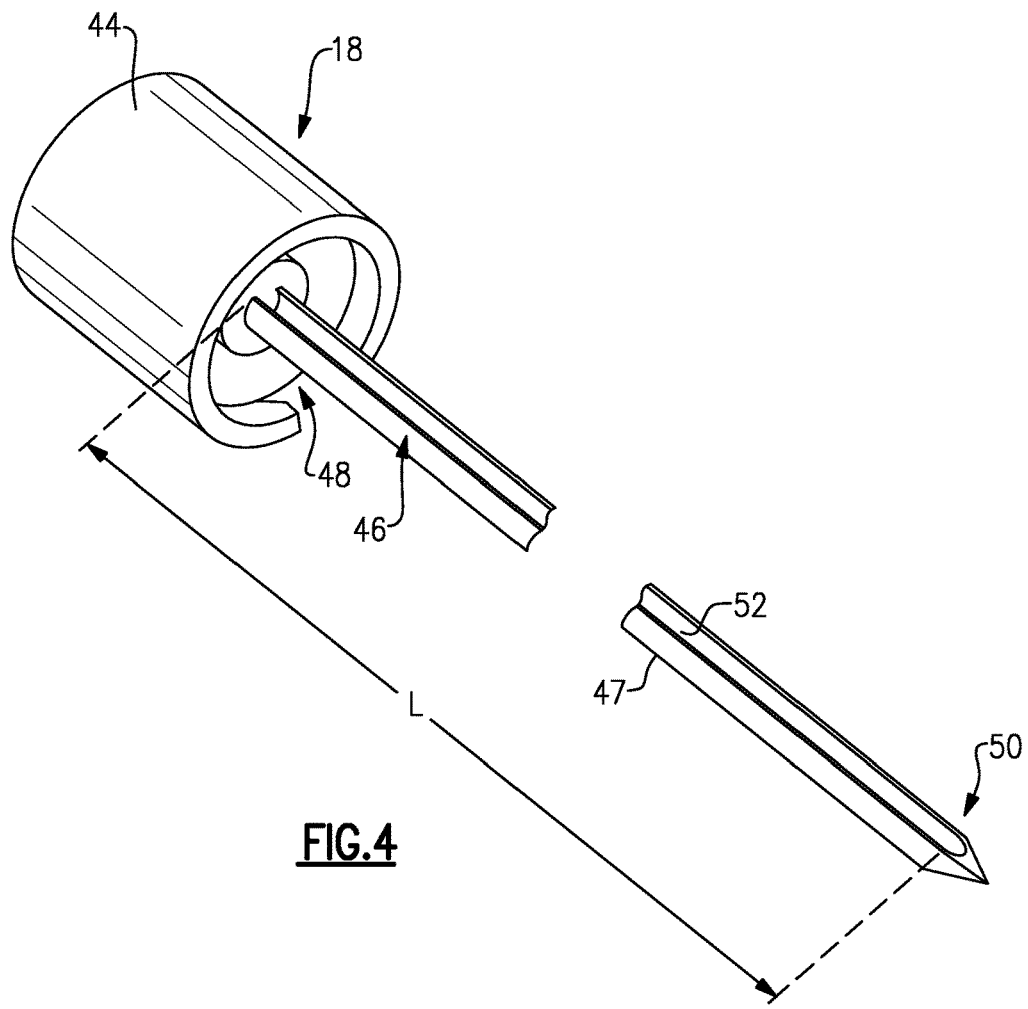
FIG. 4 illustrates a trocar of a bone marrow aspiration needle assembly.

FIG. 4 illustrates a trocar 18 of a bone marrow aspiration needle assembly 10. The trocar 18 includes a cap 44 and a shaft 46 connected to the cap 44. The shaft 46 extends between a proximal portion 48 and a tip portion 50. The proximal portion 48 may be connected to the cap 44, and the tip portion 50 may be pointed to facilitate penetrating bone.

The shaft 46 of the trocar 18 may include a groove 52 that extends longitudinally across a length L of the shaft 46. The groove 52 may be formed in an outer surface 47 of the shaft 46. In one embodiment, the groove 52 extends radially into the shaft 46.

Figure 5:
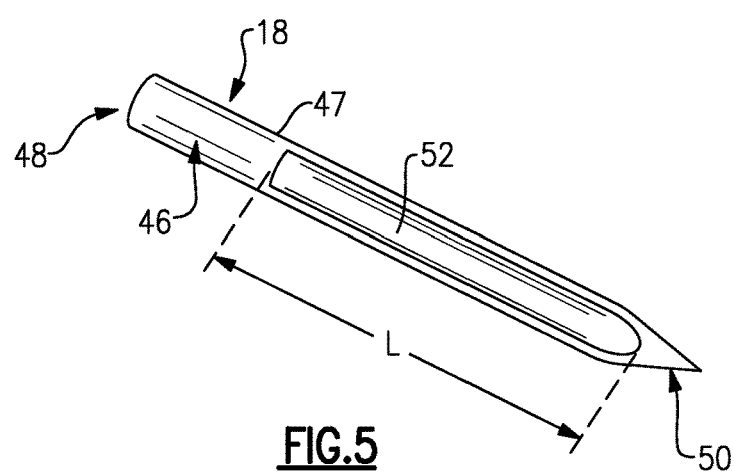
FIG. 5 illustrates another trocar.

In one non-limiting embodiment, the length L of the groove 52 spans the entire distance from the tip portion 50 to the proximal portion 48. In another embodiment, the length L of the groove 52 spans only a portion of the distance between the tip portion 50 and the proximal portion 48 (see FIG. 5). In both of these embodiments, the groove 52 is not localized at the tip portion 50 but extends at least partially into a central body of the shaft 46 that is between the proximal portion 48 and the tip portion 50. As discussed in greater detail below, the groove 52 equalizes pressure gradients that may occur between a bone marrow space inside of bone and an ambient space outside of bone to alleviate pain associated with a bone marrow aspiration procedure. For example, pain is often associated with removing the trocar 18 from the cannula 16 of the needle assembly 10 (see, e.g., FIG. 1 and FIG. 7B).

Figure 6A:
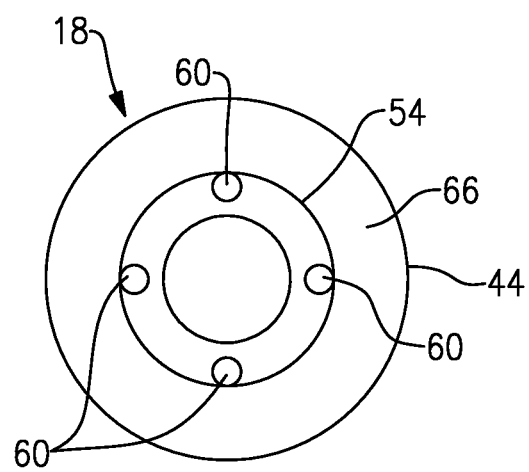
FIGS. 6A and 6B illustrate exemplary adapters of a trocar cap of a bone marrow aspiration needle assembly.
Figure 6B:
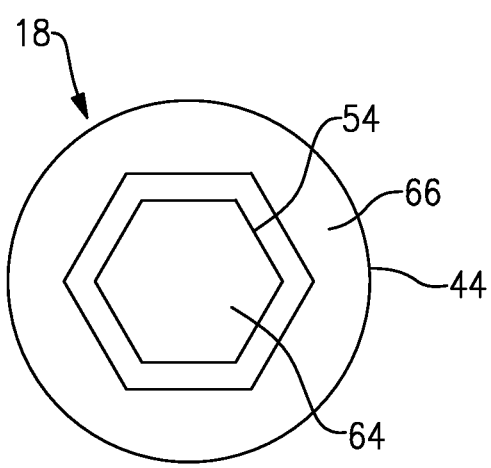

Referring to FIGS. 6A and 6B, the cap 44 of the trocar 18 may include an adapter 54. The adaptor 54 may be located on a top face 66 of the cap 44 and accommodates an insertion tool, such as a drill or other insertion tool. In one embodiment, the adaptor 54 includes a plurality of pin openings 60 for connecting to an insertion tool (see FIG. 6A). In another embodiment, the adaptor 54 includes a recessed opening 64 for accepting an insertion tool. The recessed opening 64 may include a hexagonal shape, in one non-limiting embodiment. Other shapes are also contemplated within the scope of this disclosure.

FIGS. 7A-7D, with continued reference to FIGS. 1-6B, schematically illustrate an exemplary method for aspirating a bone marrow sample from a bone. The bone marrow aspiration needle assembly 10 may be used to aspirate bone marrow from any bone. However, the following exemplary method is illustrated and described with reference to a human pelvic bone. In addition, the exemplary method is not limited to the exact order described below, and a person of ordinary skill in the art would recognize that additional or fewer steps may be necessary to obtain a bone marrow sample from the bone.

Figure 7A:
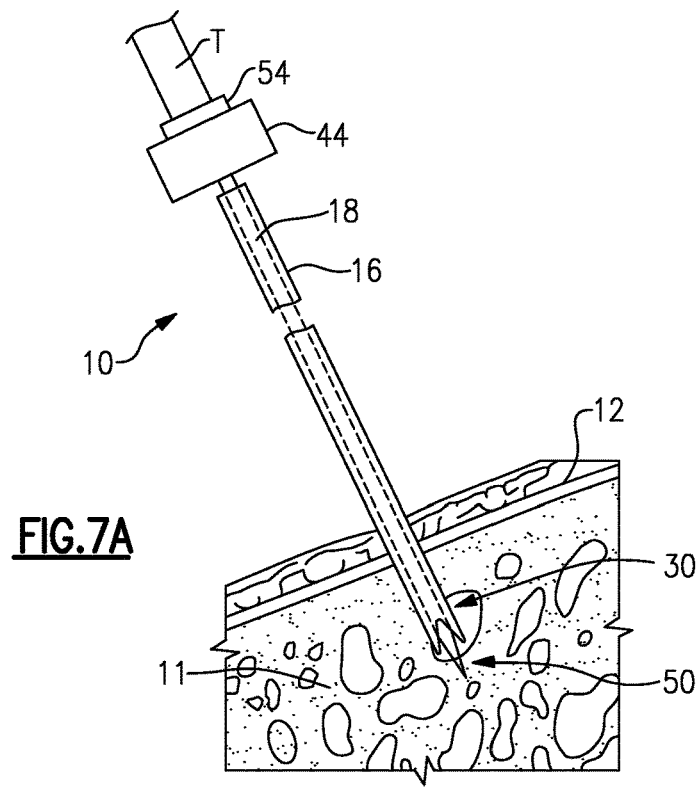
FIGS. 7A, 7B, 7C and 7D schematically illustrate a method of harvesting a bone marrow sample using a bone marrow aspiration needle assembly.

Referring to FIG. 7A, once an insertion location is selected and the site is prepared for the extraction process (measurements, markings, anesthetics, etc.), the needle assembly 10 is inserted into a bone marrow space 11 inside a bone 12. The needle assembly 10 may be pushed-in by hand, hammered in, or drilled into the bone marrow space 11 using an insertion tool T. In one non-limiting embodiment, if an insertion tool T is used for insertion, the handle 14 (see FIG. 1) may first be removed from the needle assembly 10 prior to attaching the insertion tool T to the adaptor 54 of the cap 44 of the trocar 18. The distal portion 30 of the cannula 16 and the tip portion 50 of the trocar 18 facilitate insertion of the needle assembly 10 into the bone marrow space 11.

Figure 7B:
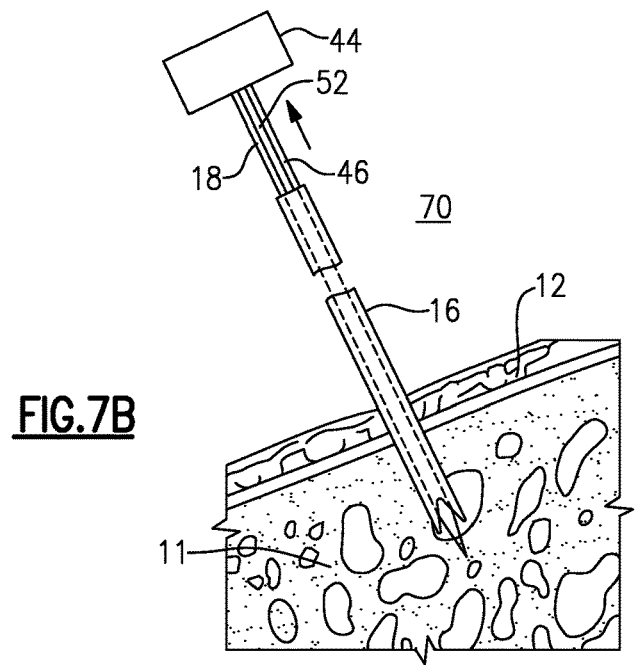

Next, as illustrated by FIG. 7B, the trocar 18 of the needle assembly 10 is removed from the cannula 16. The cap 44 of the trocar 18 may need disconnected from the handle 14 of the needle assembly 10 (see FIG. 1) prior to removing the trocar 18. The cannula 16 remains inserted inside the bone marrow space 11. During removal of the trocar 18, the groove 52 of the shaft 46 of the trocar 18 equalizes a pressure gradient between the bone marrow space 11 and an ambient space 70 outside of the bone 12. This reduces the amount of pain experienced by the patient during the bone marrow biopsy, particularly during removal of the trocar 18.

Figure 7C:
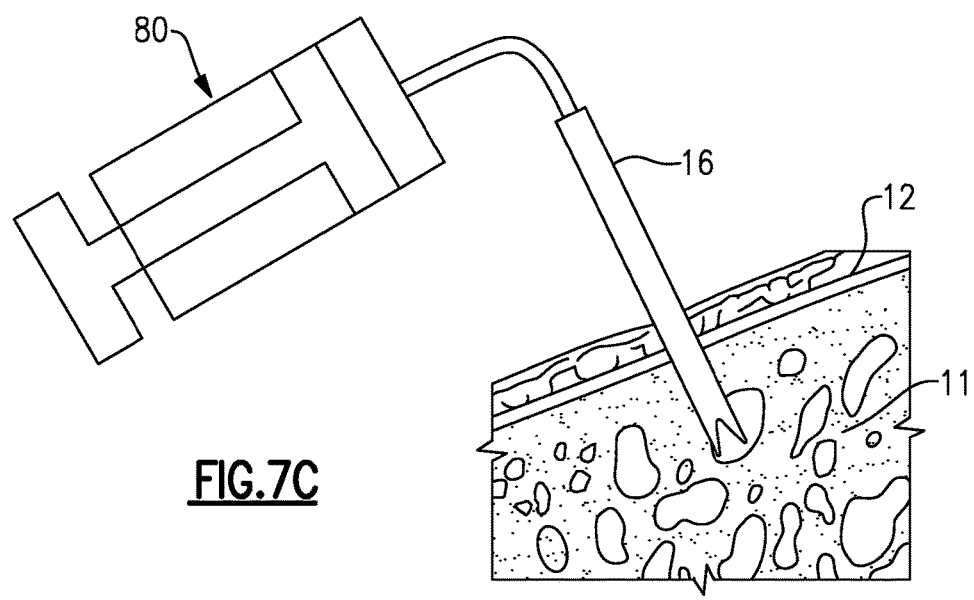
Figure 7D:
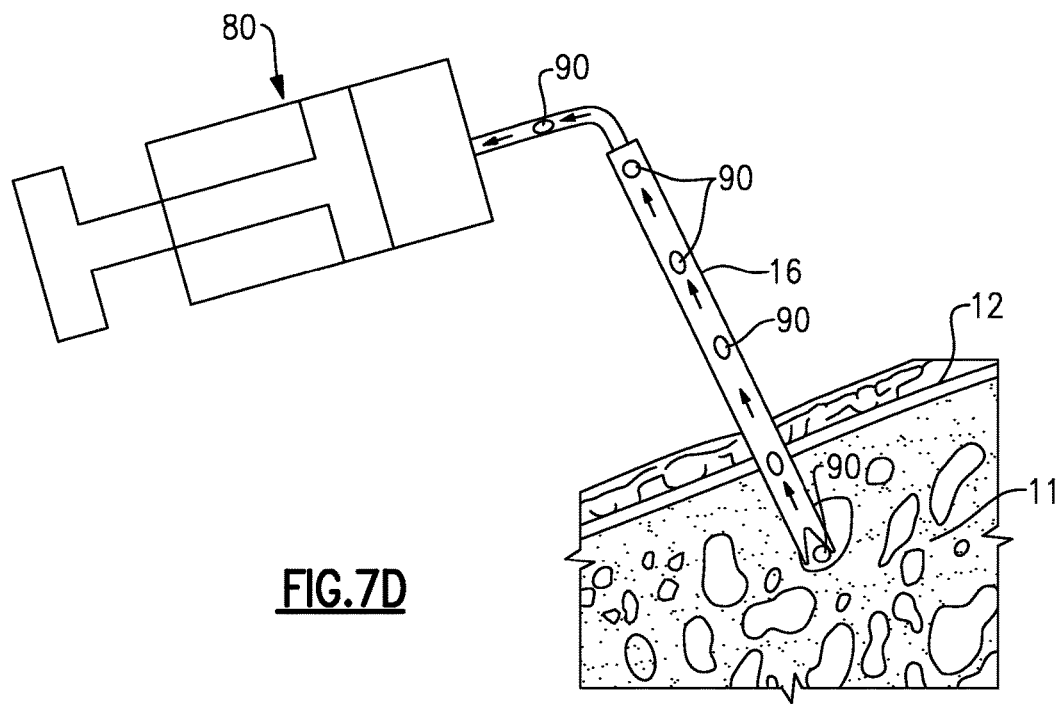

An extraction device 80, such as a syringe, may next be inserted through the cannula 16 as shown in FIG. 7C. The extraction device 80 can then be employed to draw a bone marrow sample 90 into the extraction device (see FIG. 7D). The bone marrow sample 90 may then be removed and analyzed as desired.

Figure 8:
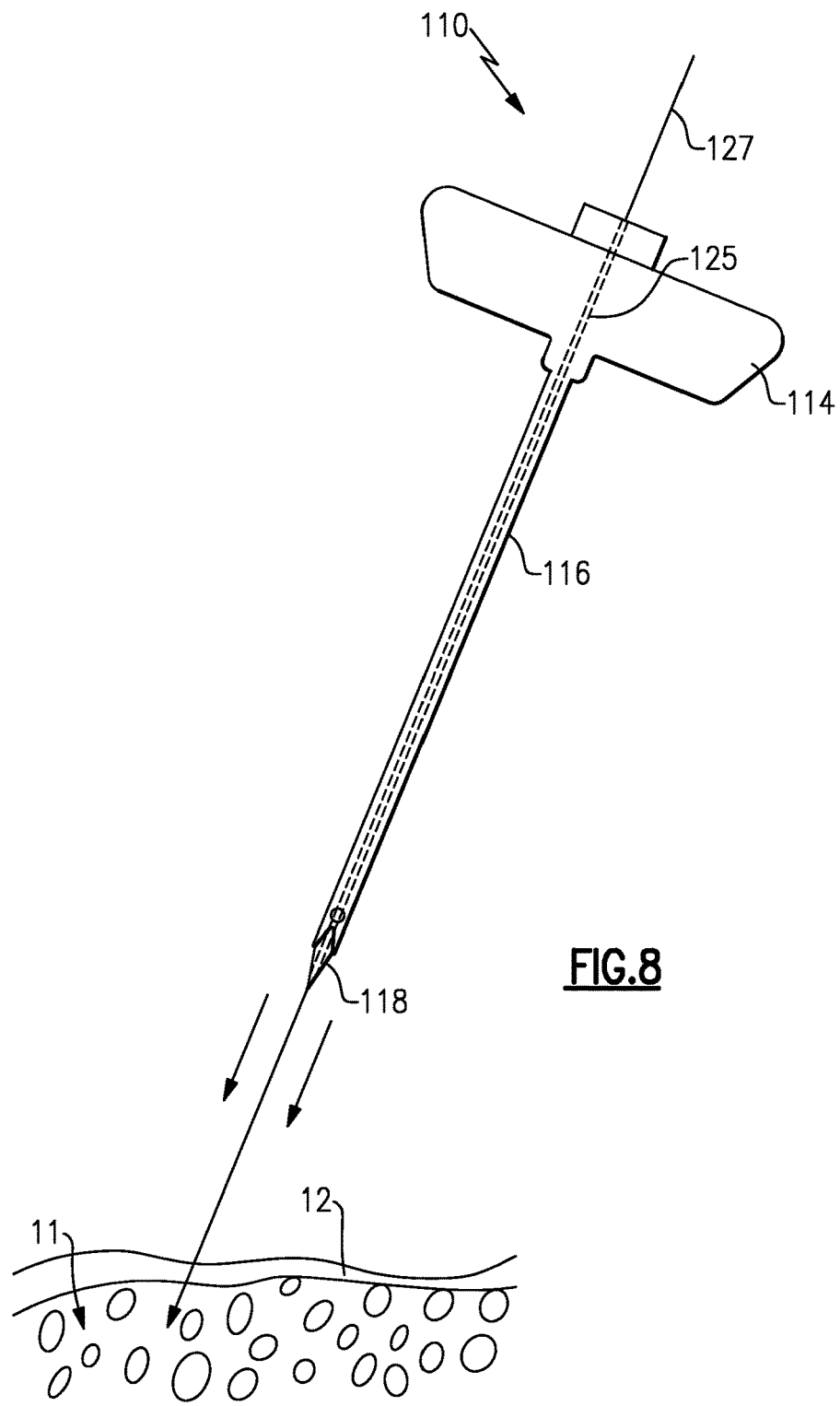
FIG. 8 illustrates a bone marrow needle assembly according to another embodiment of this disclosure.

FIG. 8 illustrates another bone marrow aspiration needle assembly 110. In this disclosure, like reference numbers designate like elements where appropriate and reference numerals with the addition of 100 or multiples thereof designate modified elements that are understood to incorporate the same features and benefits of the corresponding original elements.

The needle assembly 110 is similar to the needle assembly 10 of FIG. 1 and includes a handle 114, a cannula 116 connected to the handle 114, and a trocar 118 that can be inserted through the cannula 116. The trocar 118 may also be grooved. However, in this embodiment, the trocar 118 includes a central lumen 125 that extends through the trocar 118. The needle assembly 110 may be inserted over a wire 127, such as a k-wire, via the central lumen 125 to provide targeted insertion of the needle assembly 110 into a bone marrow space 11 of a bone 12.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A needle assembly, comprising:
    a cannula;
    a trocar separate from and insertable through said cannula, said trocar including a cap, a shaft connected to said cap, and a central lumen extending through said cap and said shaft, wherein said shaft extends longitudinally between a proximal portion of said shaft and a tip portion of said shaft;
    a groove formed in an outer surface of said shaft and extending to said cap, wherein said groove extends radially into said shaft and is linear along an entire longitudinal length of said groove; and
    a k-wire insertable through said central lumen.

2. The assembly as recited in claim 1, wherein said groove extends across an entire length of said trocar.

3. The assembly as recited in claim 1, wherein said groove extends from said tip portion to said proximal portion.

4. The assembly as recited in claim 1, wherein said tip portion includes a pointed tip.

5. The assembly as recited in claim 1, wherein said cannula is removably connected to a handle.

6. The assembly as recited in claim 1, wherein said cannula includes a plurality of depth markings and a plurality of side ports.

7. The assembly as recited in claim 1, wherein said cannula includes a distal portion having a forked tip.

8. The assembly as recited in claim 1, comprising an adaptor disposed on said cap and configured to receive an insertion tool.

9. The assembly as recited in claim 1, comprising an extraction device insertable through said cannula after removing said trocar.

10. The assembly as recited in claim 1, wherein said groove is configured to equalize a pressure gradient between a bone marrow space and an ambient space during removal of said trocar from said cannula when said needle assembly is inserted into the bone marrow space.

11. The assembly as recited in claim 1, wherein said needle assembly is configured such that, in use, said groove extends to a location outside of a bone when said needle assembly is inserted into a bone marrow space.

12. The assembly as recited in claim 1, wherein said needle assembly is configured such that, in use, said longitudinal length of said groove extends from a bone marrow space to an ambient space outside of bone containing the bone marrow space when said trocar is positioned within said bone marrow space.

13. A bone marrow aspiration needle assembly, comprising:
    a handle;
    a cannula connected to said handle; and
    a trocar separate from and insertable into said cannula, said trocar including a cap and a shaft connected to said cap, wherein a groove extends along an outer surface of said shaft and extends longitudinally across an entire length of said shaft and is linear along the entire length, wherein said groove is configured to equalize a pressure gradient between a bone marrow space and an ambient space during removal of said trocar from said cannula; and
    a k-wire insertable through a central lumen of said trocar.

14. A surgical method, comprising:
    inserting a needle assembly into a bone marrow space inside a bone, the needle assembly including a cannula and a grooved trocar received through the cannula, the grooved trocar including a groove that extends longitudinally across an entire length of a shaft of the grooved trocar, the groove extending outside of the bone when the needle assembly is inserted into the bone marrow space; and
    equalizing a pressure gradient between the bone marrow space and an ambient space outside of the bone with the grooved trocar as the grooved trocar is removed from the cannula.

15. The surgical method as recited in claim 14, wherein the inserting step includes connecting an insertion tool to an adaptor of the grooved trocar and drilling the needle assembly into the bone marrow space.

16. The surgical method as recited in claim 14, comprising disconnecting a cap of the grooved trocar from a handle of the needle assembly prior to removing the grooved trocar from the cannula.

17. The surgical method as recited in claim 14, comprising inserting an extraction tool into the cannula after removing the grooved trocar.

18. The surgical method as recited in claim 14, wherein the inserting step includes positioning the needle assembly over a wire via a central lumen that extends through the grooved trocar.

* * * * *